(12) United States Patent
Lichtman et al.

(10) Patent No.: US 11,213,234 B1
(45) Date of Patent: Jan. 4, 2022

(54) IMAGED-BASED UROFLOWMETRY DEVICE

(71) Applicants: Zavdi Lichtman, San Jose, CA (US); Joseph Drori, San Jose, CA (US)

(72) Inventors: Zavdi Lichtman, San Jose, CA (US); Joseph Drori, San Jose, CA (US)

( * ) Notice: Subject to any disclaimer, the term of this patent is extended or adjusted under 35 U.S.C. 154(b) by 0 days.

(21) Appl. No.: 17/336,587

(22) Filed: Jun. 2, 2021

(30) Foreign Application Priority Data

Jun. 30, 2020 (IL) .......................................... 275760

(51) Int. Cl.
| | | |
|---|---|---|
| *G06T 7/62* | (2017.01) | |
| *A61B 5/20* | (2006.01) | |
| *H04N 7/18* | (2006.01) | |
| *G01F 1/66* | (2006.01) | |
| *G06T 7/246* | (2017.01) | |
| *H04N 5/33* | (2006.01) | |
| *G06T 7/00* | (2017.01) | |

(52) U.S. Cl.
CPC .............. *A61B 5/208* (2013.01); *G01F 1/661* (2013.01); *G06T 7/0012* (2013.01); *G06T 7/248* (2017.01); *G06T 7/62* (2017.01); *H04N 5/33* (2013.01); *H04N 7/181* (2013.01); *H04N 7/188* (2013.01); *G06T 2207/10016* (2013.01); *G06T 2207/10048* (2013.01); *G06T 2207/30004* (2013.01)

(58) Field of Classification Search
None
See application file for complete search history.

(56) References Cited

U.S. PATENT DOCUMENTS

| | | | | |
|---|---|---|---|---|
| 2017/0303901 | A1* | 10/2017 | Sekine | ............... G01N 33/4833 |
| 2018/0331078 | A1* | 11/2018 | Gould | ..................... H01L 33/54 |
| 2019/0365307 | A1* | 12/2019 | Laing | ..................... A61B 5/205 |
| 2020/0268303 | A1* | 8/2020 | Oliva | ................... A61B 5/0022 |

\* cited by examiner

*Primary Examiner* — Eileen M Adams

(57) ABSTRACT

It is a principal goal of the present invention is to provide a uroflowmetry device for calculating uroflowmetry data (flow rate and other data) associated with urination sessions. The invention is an in-toilet uroflowmetry device, which unlike existing stand-alone and in-toilet devices is not touched by the urine stream, and un-like with existing in-toilet devices, the toilet is useable for all normal functions by men and women.
The invention also provides new data not provided by existing uroflowmetry devices.
The present invention is a device comprised of an electronic open loop belt with video cameras, a single-board computer (SBC), LEDs and various sensors to start the video cameras and control the LEDs. The video data is transferred wirelessly to a website where image processing is performed on the video data, followed by computations of flow rate and additional uroflowmetry data.

5 Claims, 4 Drawing Sheets

| Date | Drink | | | Urine | | Leakage | | |
|---|---|---|---|---|---|---|---|---|
| Time | Type | How much (mls) | Volume of Urine (mls) | How Urgent 0-5 5=most urgent | Leakage with Urgency | Leakage with activities | Pad change | |
| | | | | | | | | |
| | | | | | | | | |
| | | | | | | | | |

| Date | Drink | | Urine | | Leakage | | |
|---|---|---|---|---|---|---|---|
| Time | Type | How much (mls) | Volume of Urine (mls) | How Urgent 0-3 3= most urgent | Leakage with Urgency | Leakage with activities | Pad change |
| | | | | | | | |
| | | | | | | | |
Fig. 1
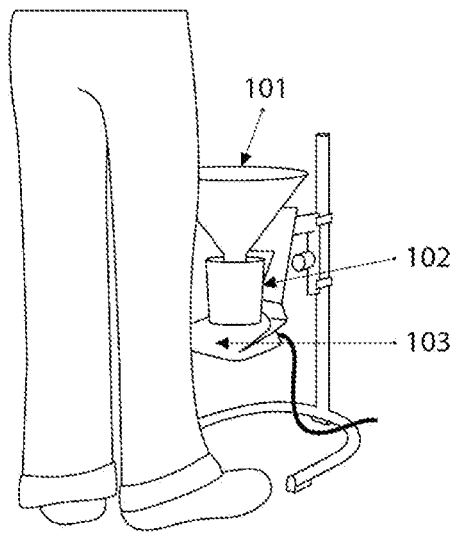
Fig. 2a
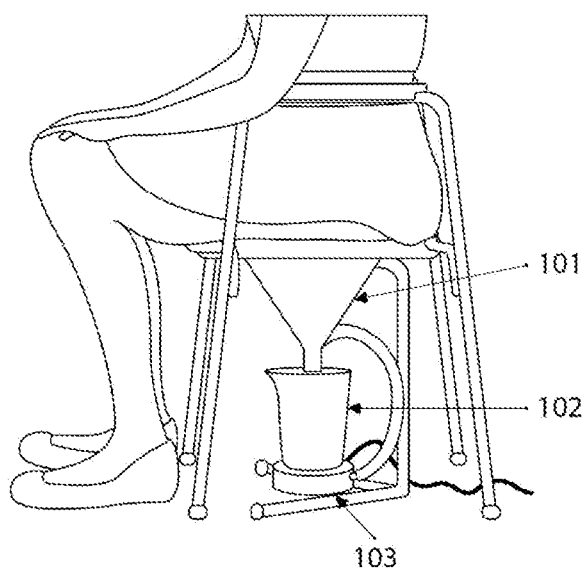
Fig. 2b

| HW#/Fig. # | SBC Single Board Computer | Battery & Charge Cable | Cameras | LEDs & Light Sensors | Motion & Sound Sensors | Functionality |
|---|---|---|---|---|---|---|
| HW1/Fig. 4 | Y | Y | Y | | | Men standing only. Start with a phone app. |
| HW2/Fig. 5 | Y | Y | Y | | Y | Men standing only. Auto-start. |
| HW3/Fig. 6 | Y | Y | Y | Y | | Standing and sitting. Start with a phone app. |
| HW4/Fig. 7 | Y | Y | Y | Y | Y | Standing and sitting. Auto-start. |

IMAGED-BASED UROFLOWMETRY DEVICE

BACKGROUND OF THE INVENTION

The field of the invention relates generally to the need for uroflowimetry data, as volume and flow rate, for urination sessions by patients with certain medical conditions.

A Voiding Diary is a diary/log of urination (or voiding) sessions and liquid intake of a patient, which is typically requested by a medical practitioner such as a urologist or other physician in order to evaluate Lower Urinary Track Symptoms (LUTS). LUTS refers to a group of clinical symptoms involving the bladder, urinary sphincter, urethra, and in men, the prostate. These symptoms commonly relate to conditions that affect men but are also relevant to women. There are many medical conditions that cause LUTS, including, BPH (Benign Prostate Hyperplasia), bladder stones, bladder cancer, prostate cancer, muscle weakness, diabetes, UTI (urinary tract infection) and more.

The prevalence of LUTS in the population is a subject of ongoing research.

According to published results, more than 50%® of men and women over the age of 50 suffer from LUTS, at least occasionally.

Ideally, a Voiding Diary is manually filled by the patient either on paper, on an online form, or on a phone app during the period of time that the patient is not in the hospital or at a clinic. The Voiding Diary helps the medical practitioner to evaluate the patient's liquid balance, bladder capacity and function, and relate this data to LUTS and the medical conditions that cause it.

Generally, patients are asked to fill the Voiding Diary for only three days because they cannot be trusted to record every voiding session and liquid intake over a longer period of time.

A representative Voiding Diary is shown in FIG. 1 having columns for liquid intake, voiding sessions and leakage reports. The data requested for each voiding session comprises the time of voiding session and estimate of volume in mL (milliliter). Data regarding the urgency to empty the bladder, accidental leaks and activity before the voiding session are requested as well. The data requested for each liquid intake comprises the time of the liquid intake, type of liquid (e.g. water, coffee, soda, etc.) and volume in mL.

The use of Voiding Diaries demonstrates the critical need to get patient uroflowmetry data. But the manual Voiding Diary is a very primitive solution.

The main problem with the Voiding Diary is that the accuracy of the data filled out by the patient is very low. The most important data, the urine volume, is a very inaccurate estimate by the patient. In addition, it is possible that not all voiding sessions are recorded in the Voiding Diary. Additionally, medical practitioners would prefer receiving more data than that which is provided by a Voiding Diary, as well as more accurately measured data. Uroflowmetry devices, which are used at hospitals and clinics can provide this data, including an accurate reading of volume, dynamic flow rate (in a graph), voiding session duration, etc.

The current most common uroflowmetry solution is a stand-alone apparatus using a weight-based method of recording and computing data. This apparatus comprises a funnel, a container under the funnel that accumulates the urine, and a scale under the container that measures the increased weight of the container multiple times per second throughout the voiding session. The weight measurements are converted to flow rate in mL/second.

FIGS. 2a and 2b illustrate prior art stand-alone weight-based uroflowmetry apparatuses configured for men (FIG. 2a) and women (FIG. 2b). Men can also use the configuration for women. As shown in FIGS. 2a and 2b, the funnel 101 is situated above container 102 for directing urine therein. Beneath container 102 is scale 103 for weighing container 102 and its contents. These apparatuses are typically used in hospital urology departments and in some clinics.

Prior art patent documents that describe weight-based uroflowmetry devices include U.S. Pat. No. 9,775,556 to DiMino et al. and US 20190008439 to Sageder et al.

Prior art patent documents and publications related to in-toilet image-based uroflowmetry devices include: "A mountable toilet system for personalized health monitoring via the analysis of excreta" to Park et al. Nature Biomedical Engineering Vol 4 (June 2020) 624-635, mostly about analysis of urine test strips and stool but includes a proof of concept for one possible method for image processing for urine flow rate; JP 2017217228A to Shimadzu Corp, another possible method for image processing for urine flow rate.

The weight-based method of flow rate computation uses a known formula for weight to volume conversion. Water weight is 1.0 gram per 1 cc (cubic centimeter). Urine has a bit higher density than water. If the kidneys function well, the weight of the urine is between 1.002 grams and 1.03 grams per 1 cc. But if a person suffers from uncontrolled diabetes, UTI (urinary tract infection), etc. the urine weight per cc can be higher. Weight-based uroflowmetry apparatus assumes a urine weight of about 1.05 gram per 1 cc. Therefore, the devices generally have a flow-rate accuracy of +/−5%. This covers the range from the lowest urine density of 1.002 gram for 1 cc up to 1.1 gram for 1 cc.

The measured results are transmitted wirelessly from the uroflowmetry apparatus to a remote device such as a computer or a website.

The main usability problems associated with stand-alone uroflowmetry apparatuses are that they take up a sizeable amount of space and have to be placed in a private location such as a bathroom large enough to place the apparatus. Furthermore, after each use the container needs to be manually emptied. In addition, both the funnel and the container need to be manually washed. These tasks present both hygienic and operational problems in a busy hospital urology department or a clinic.

New designs of in-toilet uroflowmetry apparatuses have been disclosed wherein the funnel is positioned in the middle of the toilet bowl without touching the water at the bottom of the bowl. The funnel is held in place by plastic part/s which sit on the toilet bowl rim. At the bottom of the funnel there is an electro-mechanical device to measure urine flow rate and time, and a communication chip to transmit the data to a remote device such as a cellphone, personal computer or a website. An example of such a device can be seen at the website https://iuflow.com/.

These new designs of in-toilet apparatuses with a funnel are aimed mainly at the home market. They eliminate the need for private space in a large bathroom, which the stand-alone device requires. Some designs enable the regular flushing of the toilet to wash the funnel.

Nevertheless, the in-toilet apparatuses with a funnel have a major usability problem. When such an apparatus is placed in a toilet, the toilet can be used only for urination. This creates a problem for homes with only one toilet, as well as in independent living centers and adult care facilities with a single toilet per unit. It is also a problem for hospitals if the goal is to place a device in the toilet of every patient's room in some departments and clinics that have only a single toilet for the patients. If the device is repeatedly taken out of the toilet, every time it is taken out it has to be washed, dried and stored.

Another usability problem of the new in-toilet apparatuses with a funnel is that if regular flushing of the toilet does not flush the funnel, the funnel has to be manually cleaned (by throwing water into it) after each use.

BRIEF SUMMARY OF THE INVENTION

It is a principal goal of the present invention is to provide a uroflowmetry device for calculating uroflowmetry data (flow rate and other data) associated with urination sessions. The invention is an in-toilet uroflowmetry device which is not touched by the urine stream and the toilet is useable for all normal functions by men and women.

The invention also provides new data not provided by existing uroflowmetry devices: velocity, diameter and a coefficient C (percent fullness of the urine stream). Clinical urology research will be required to evaluate the medical meaning of this new data.

The present invention is a device comprised of an electronic open loop belt with video cameras; a single-board computer (SBC) with a processor, data storage and a wireless communication module; battery and a charging cable (or another power source arrangement). The device has at least two video cameras but can also include one or more infrared video cameras. The belt has inside wires for communication between components and power supply to the components.

Depending on the configuration, the device can have multiple LEDs (light emitting diodes) that can also be intensity controlled LEDs along the belt, for providing light to the cameras, and at least one light sensor which can also be a light measuring sensor. Additional sensors, depending on the configuration, are motion sensors and sound sensors.

The open loop belt is flexible and can be shaped according to the contour of the rim of a toilet bowl and is removably affixed to the interior rim of the toilet bowl by clips, or hooks, or bendable soft plastic strips. In this position, the belt avoids getting wet from the water released from the tank when the toilet is flushed. The belt is open, i.e. its ends are separated from each other, in order to fit toilets of various sizes.

During a urination session, the video cameras of the device of the present invention take videos of the urine stream, preferably at 240 fps (frames per second) by each camera. Optionally, the videos are processed by video processing software on the device to reduce video data volume before being transmitted wirelessly to a website with additional data such as time-stamps, for data processing comprising of image processing followed by computations of dynamic flow rate, volume, duration, etc.

Performing the image processing and computations on a website, off the device, has the advantage that the installed base of devices always benefit from continuous improvement to the image processing and computations.

The uroflowimetry data is available on the website for the patient and his/her medical practitioner. Among other features, the medical practitioner has an option to set data dependent alerts.

The in-toilet image-based device of the present invention has usability advantages over stand-alone and in-toilet apparatuses with a funnel. First and foremost, the urine stream does not touch the device and the toilet is useable for all normal functions by men and women. The device of the present invention does not require space in a private location such as a large bathroom. The electronic belt of the present invention is easily installable and removable from the toilet for the purpose of cleaning the belt and/or the toilet.

The present invention is designed mainly for the home market, including homes with a single toilet, as well as independent living centers and adult care facilities where there is a single toilet per unit. Hospital urology departments that generally have several stand-alone devices configured for men and women, would also benefit from the installation of the image-based device of the present invention in the toilet of every patient's room. Similarly, clinics can install the image-based device in a toilet and have it available to men and women.

Activation of the device is accomplished manually or automatically. Automatic activation is accomplished by the motion and sound sensors. In configurations without motion and sound sensors, manual activation is required via a phone app.

The image processing phase calculates three characteristics of the urine stream: diameter, velocity and a coefficient C of the percent fullness by liquid of the urine stream.

The velocity is calculated between every two frames. The diameter and the coefficient C are calculated for every frame.

The velocity is calculated by using a technique similar to PIV (Particle Image Velocimetry) applied to patterns of chains of 2-4 elongated drops with mostly air between them, as seen in frames of video at 240 fps (frames per second).

The coefficient C is calculated along the urine stream as the sum of the length of the separate elongated drops divided by the length of the urine stream, which is the elongated drops plus the length of the gaps of air between the drops.

The diameter is easily calculated by images from two cameras.

The image processing phase is followed by a computational phase of three steps performed for periods of between 0.05 second to 0.2 second.

The first computational step is to compute the averages of the three values calculated by image processing.

The second computational step is to calculate the urine stream cross-sectional area from the diameter.

In the third computational step, after the cross-sectional area, the velocity and the coefficient C of the urine stream are available, it is simple to compute dynamically the flow rate. The volume and additional desired data are calculated from the flow rate.

Preferably, the operation of the device is unaffected due to getting wet by a liquid such as urine and water, but the cameras must be kept clean.

It is a principal goal of the present invention to provide a method of calculating uroflowmetry data associated with urination sessions by a user. The method preferably comprises the steps of:
 a. installation of the device in a toilet;
 b. activating the device automatically or with a phone app;
 c. capturing videos of a urine stream via video cameras;
 d. optionally processing the videos on the device to reduce the volume of the video data;
 e. transmitting wirelessly the video data to a website for data processing (image processing followed by computations);
 f. performing on the website image processing to obtain velocity, diameter and the coefficient C, followed by computations to obtain flow rate and other uroflowimetry data;

g. storing the resulting uroflowmetry data in the user account on the website, for access by the user and his/her medical practitioner; and, h. providing a notification regarding the wellness of the user to the user and/or the medical practitioner if criteria for such alerts were set.

Optionally, the installation of the device comprises one or more of the following steps:

a. physically positioning the device on the interior of the rim of a toilet;

b. adjusting the video cameras to a desired angle;

c. calibrating the video cameras according to the size of the toilet bowl; and, d. completing a setup task to define and identify the users of the device.

Optionally, the automatic device activation comprises the steps of:

a. standby activation; and, b. start the video cameras.

Preferably, one or more of the images are saved on a website for review.

The step of performing automatic periodic testing of the cameras to determine proper cleanliness and operation is optionally provided.

BRIEF DESCRIPTION OF THE DRAWINGS

FIG. 1 shows an example of a Voiding Diary.

FIGS. 2a and 2b show two stand-alone, weight-based uroflowmetry devices configured for men (FIG. 2a) and women (FIG. 2b).

DETAILED DESCRIPTION OF THE INVENTION

The invention is an in-toilet image-based uroflowmetry device for calculating uroflowmetry data associated with urination sessions. It is a device comprised of an electronic open loop belt with wires inside for communication and power supply, and with video cameras, single-board computer (SBC) with processor, storage, wireless communication and additional components, battery and a charging cable. Optional components, depending on configuration, are LEDs (light emitting diodes), the LED's can be intensity controlled LEDs. Optional sensors, depending on configuration, are light sensors that can be also light measuring sensors for controlling the intensity of the LEDs, and motion and sound sensors for activation and deactivation of the video cameras.

Figures 3, 4:
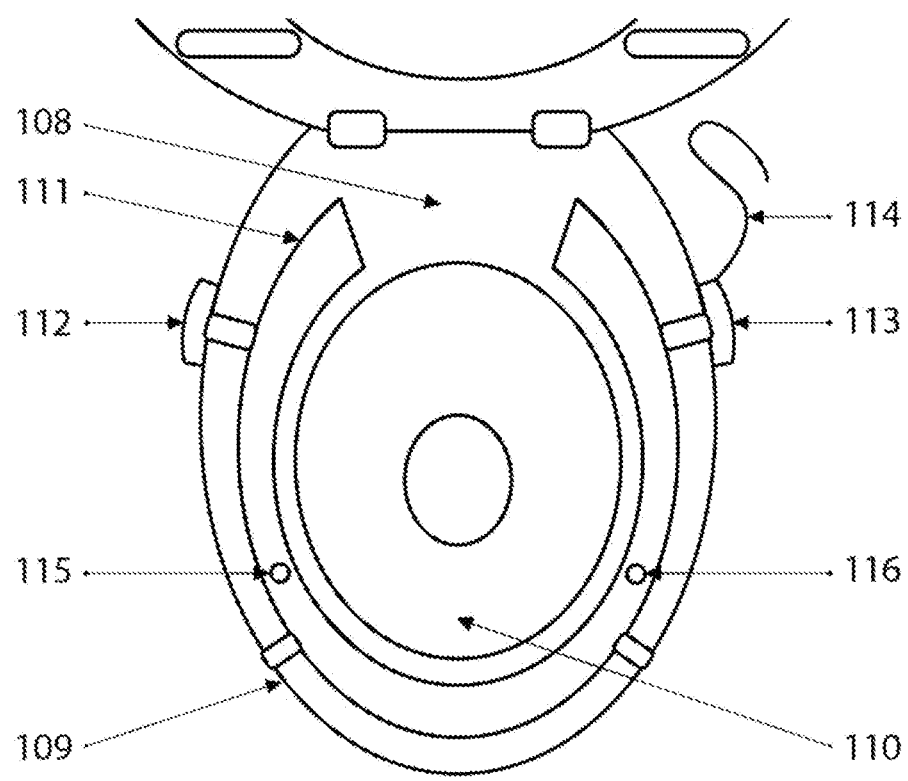
FIG. 3 shows a table of the hardware configurations and functionalities of the image-based uroflowmetry device of the present invention. It includes four hardware configurations HW1-HW4.
FIG. 4 is a drawing of HW1 configuration of the device, with functionality for men standing only and a device start with a phone app.

FIG. 3 is a table with the device's four hardware configurations and their functionalities. FIGS. 4, 5, 6 and 7 are the four device configurations.

As an example, all device configurations in the figures have two video cameras, but the device can have more than two video cameras. There is also an option, not shown in the figures, for one or more infrared video cameras to capture data that infrared cameras may capture better than regular cameras.

As an example, the device configurations show a single sensor of each type (light, motion and sound), but the device can have more than one sensor of each type. Additionally, all device configurations show a rechargeable battery and a charging cable, but there are other options as a replaceable non-rechargeable battery, or an external power source.

The electronic open loop belt is flexible to fit the interior contour of the rim of a toilet bowl, without damage to the wires inside. It is removably affixed to the interior rim of the toilet bowl by clips, hooks or bendable soft plastic strips. In this position, the belt avoids getting wet from the water released from the tank when the toilet is flushed. The belt is open, i.e. its ends are separated from each other, in order to fit toilets of various sizes.

The belt is easily removed, in order to clean the toilet and/or the belt and is easily reinstalled.

During a urination session, the video cameras take videos of the urine stream, preferably at 240 fps (frames per second) by each video camera. Optionally the videos are processed on the device by video processing software to reduce the video data volume. The videos are transmitted wirelessly to a website for data processing. The data processing is comprised of image processing followed by computations of dynamic flow rate, volume, duration, etc.

Performing the image processing and computations on a website, off the device, has the advantage that the installed base of devices always benefit from continuous improvement to the image processing and computations.

A few pictures are saved on the website. Automatic alerts are generated if these pictures contain blood or a high level of white particles. This might be important for the medical practitioner. Stand-alone and current in-toilet devices with a funnel do not provide this data.

All device hardware configurations in FIGS. 4, 5, 6, and 7 show 108 the toilet, 109 the toilet rim and 110 the toilet bowl. They have the following components that exist in every configuration:

111 the belt itself

112 the SBC (single board computer) with processor, storage and wireless communication module.

113 the battery and 114 a charging cable

115 and 116 video cameras.

Figure 6:
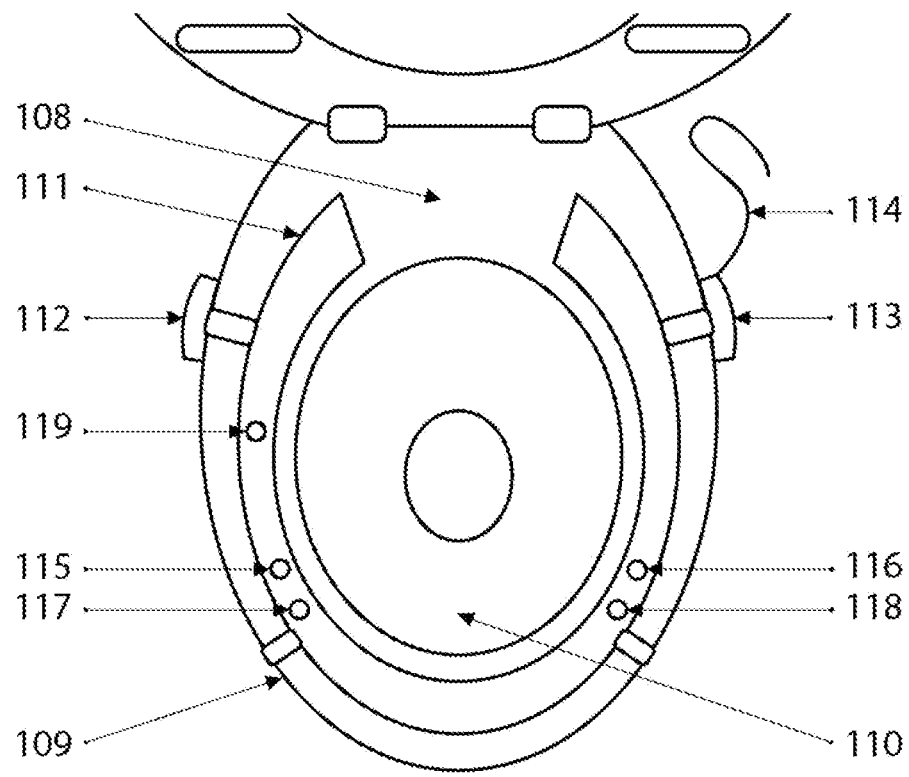
FIG. 6 is a drawing of HW3 configuration of the device, with functionality for standing and sitting and a device start with a phone app.
Figure 7:
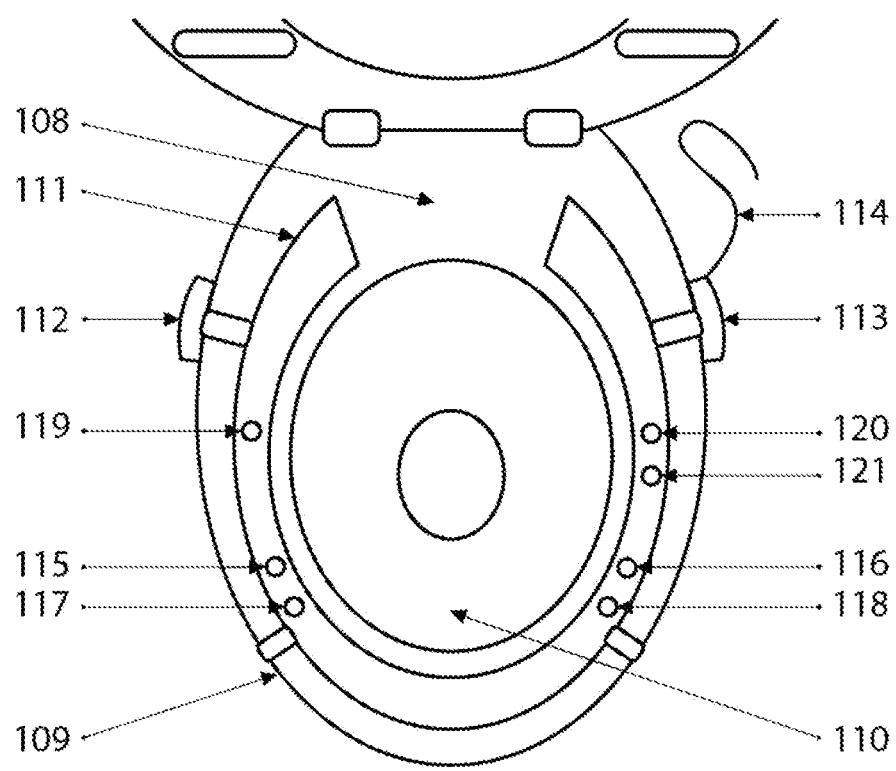
FIG. 7 is a drawing of HW4 configuration of the device, with functionality for standing and sitting and an auto-start.

The device's optional components, depending on configuration, are:

117 and 118 LEDs in FIGS. 6 and 7.

119 a light sensor, in FIGS. 6 and 7. The light sensor turns on the LEDs when there is not enough light inside the toilet. The light sensor can also be a measuring light sensor that controls the light intensity of the LEDs for optimal lighting for the videos.

Figure 5:
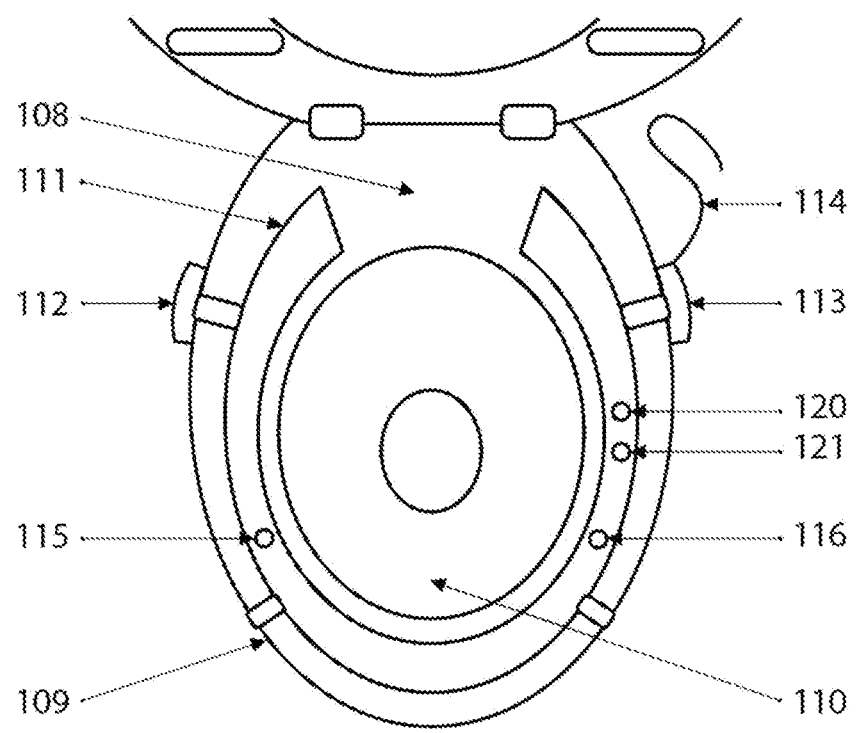
FIG. 5 is a drawing of HW2 configuration of the device, with functionality for men standing only and an auto-start.

120 a motion sensor and 121 a sound sensor, in FIGS. 5 and 7.

The data storage is one of: internal memory, a removable memory card, or a fixed storage such as an SSD (Solid State Drive).

The power source is optionally chosen from one of: a non-rechargeable battery that has to be replaced when empty, a rechargeable battery with a charging cable, or an external power source. Optionally, the belt comprises a power cable extending therefrom and plugging into an electrical outlet or connecting with an external power source.

The wireless communication module of the device supports three communication methods: wifi and cellular communication between the device and a website, and Bluetooth for communication between the device and a phone app.

The motion and sound sensors are used to auto-start the device. In configuration without motion and sound sensors, the user activates the device using a phone app.

FIG. 4 shows HW1 configuration. It is the simplest configuration.

It has only the belt itself 111, the SBC 112, the battery 113, the charging cable 114 and two video cameras 115 and 116. HW1 functionality is for men standing only and device start with a phone app.

FIG. 5 shows HW2 configuration which adds to HW1 configuration the motion and sound sensors 120 and 121. HW2 functionality is for men standing only with auto-start of the device.

FIG. 6 shows HW3 configuration which adds to HW1 configuration the 2 LEDs 117 and 118, and the light sensor 119. HW3 functionality is for standing and sitting. The device is started with a phone app.

FIG. 7 shows HW4 configuration, which is the full configuration with all the optional components. HW4 functionality is for standing and sitting with auto-start of the device.

It is important to note that the position of each component on the belt 111 is shown in FIGS. 4-7 for illustrative purposes only. Depending on factors such as design, engineering, etc., it may be advantageous to consider other configurations and positioning of components. It is also possible that due to engineering considerations more than one SBC will be used, one for each camera.

The device uses software on the device itself, on a website and in a phone app. Some tasks can be performed by the user either on the website or with the phone app.

The main modules of software on the device itself are:

Management and control software for the electronic belt components.

Device installation task, to help the user install the device.

Setup task to define if single user, multi-user, possible guest use, etc.

Optional Video processing software for the videos taken by the video cameras, to reduce the video data volume for transmission to the website.

Wireless transmission of the videos and additional data to the website.

Automatic periodic tests of the video cameras to test if the lenses are clean and alert the user if the lenses require cleaning.

The device communicates with the website via wifi or cellular communication and with the phone app via Bluetooth communication. All device communications are 2-way.

The main modules of software on the website are:

Image-processing applied to the video data transmitted wirelessly by the SBC of the device, calculating dynamically for the urine stream: diameter, velocity and the coefficient C, percent fullness of the urine stream with liquid.

Software for computing flow rate, volume, and other data from the diameter, velocity and the coefficient C provided by the image processing software.

Database software.

Management software for access, viewing results, alert setup, alert delivery, etc. for both the user and the medical practitioner.

User ability to add voiding session info such as level of urgency, if leakage occurred, etc., as well as info about liquid intake.

Setup task to define if the device use is by a single user, few users, possible guest, and user IDs.

The phone app software includes the following main tasks:

Device installation task to help the user install the device.

Setup task to define if the device use is by a single user, a few users, possible guest and user IDs.

Access to the user data on the website including receiving of alerts.

User ability to add voiding session info such as level of urgency, if leakage occurred, etc., as well as info about liquid intake.

The phone app communicates with the website via wifi or cellular communication and with the device via Bluetooth communication.

The device, which has software on the device itself, with the website and the phone app is a complex system. The following are a few of the tasks that such a system requires, described in detail.

The device installation task uses the phone app and software on the device. This task guides the user in the process of physical installation of the device on the interior rim of the toilet bowl. Using the software, the user adjusts the video cameras at a small downward angle, so the top boundary of every video taken is under the rim across from each camera. After adjustment of the video cameras at the required angle, a calibration step is automatically performed to tune the video cameras for the exact size of the toilet bowl.

The device setup task is performed following the initial device installation.

In this task, the user defines important aspects of the device operation.

First, the user defines if the device is for a single user or more (multi-user) and then enters the name/s and/or other ID/s. Second, the user defines if guest use of the device is expected. This is important in auto-start configurations of the device. This task can be performed either on the website or with the phone app.

User ID is important in order to attribute the uroflowmetry data to the right person. It is simple in devices started by a phone app. In devices with auto-start, there are a few situations. In a single user and no guest setup, user ID is automatic. In setups with guest use and/or multi-user, user ID can be entered in the app before the session. User ID can also be entered in the app or on the website after the auto-started session, with the ability to delete the session data if it belongs to a guest.

Optional processing of the videos on the device reduces the volume of data transmitted from the device to the website.

The device storage is chosen from one of: internal memory, removable memory card or a fixed storage such as an SSD (Solid State Drive).

The two wireless transmission methods from the device to the website are:

1. Via wifi to a router, followed by upload from the router to the website.

2. Via cellular communication directly from the device to the website.

In the first transmission method, wifi speed depends on the distance of the device from the router and the router generation and technology. The second step of this method can also be slow. In some current Internet communication technology, upload speed is about 5%40% of download speed.

In the second transmission method, via cellular communication, current 4G cellular technology (which has a few variations) provides a relatively slow speed. This method might be more viable when 5G cellular technology matures and becomes available.

In cellular communication, as in wifi, generally upload speed is about 5%-10% of download speed. In addition, in cellular communication actual speeds can be 1%-10% of theoretical speeds, with great variations.

Image processing is central to the device's functionality. Possibly, no existing device or system uses image processing on a liquid stream free in-the-air. But there is no technology gap precluding it.

The image processing phase calculates dynamically three characteristics of the urine stream: diameter D, velocity VL and a coefficient C of the percent of fullness of the urine stream with liquid.

Velocity is calculated between every two video frames, while diameter and the coefficient C are calculated per each frame.

The diameter D of a urine stream is generally between 3 mm to 6 mm. With at least two cameras from different directions aimed at the urine stream, it is simple to calculate dynamically the diameter. In case of a split urine stream, the diameter of each sub-stream is calculated separately and multiple diameters are provided for the following computations. If the stream/sure not exactly round, an equivalent computed diameter is calculated.

The velocity in cm/second is calculated by a procedure similar to the technique of PIV (Particle Image Velocimetry) applied to patterns of chains of 2-4 elongated drops with mostly air between them. These patterns of chains of drops appear clearly in video at 240 fps (frames per second).

The coefficient C is calculated along the urine stream as the sum of the length of the separate elongated drops in a frame, divided by the length of the urine stream in the frame which is the length of the drops plus the length of the gaps between the drops.

After the diameter D (in mm), the velocity VL (in cm/sec) and the coefficient C are available. It is possible to compute flow rate in mL/sec (milliliter per second).

This is done for periods of between 0.05 second to 0.2 second in the computational phase that includes three steps. For videos at 240 fps, periods of 0.05 second (20 times per sec) have 12 frames, while periods of 0.2 second (5 times per second) have 48 frames. Optionally, longer periods of time, up to 0.2 second, are used at the beginning and end of the urination session when the velocity and flow rate are relatively slow, and shorter period of time are used in the middle of the urination session when the velocity and flow rate are faster.

First, compute averages for velocity, diameter and the coefficient C obtained via image processing, for successive frames.

Second, compute the cross-sectional area of the urine stream from the diameter: $A=\pi r^2$.

Third, Compute flow rate Q: $Q=VL \times A \times C$.

In the case of a split urine stream and therefore multiple diameters, one for each sub-stream, the cross-sectional area is computed separately for each sub-stream. The area A is the summation of the areas computed for all the sub-streams.

An example for a specific period of between 0.05 second to 0.2 second:

For velocity VL=200 cm/sec, diameter D=4.6 mm and coefficient C=0.5.

$A=3.14159 \times 2.3 \times 2.3 = 16.619$ square mm=0.16619 square cm.

$Q=200 \times 0.16619 \times 0.5 = 16.619$ mL/sec.

Flow rate varies dynamically during the urination session, starting low, increasing to a maximum and then decreasing until the session ends.

For adults over 50, the maximum flow rate is generally up to 25 mL/sec.

The urination session volume VV (voiding volume) and all other data are computed from the dynamic flow rate over the urination session duration.

All the data computed for each urination session is saved on the website, for the user and his/her medical practitioner to view. The data item names used below are the common names used by urologists. But D, VL and C are currently not available to urologists. Clinical urology research will be required to evaluate the medical meaning of this new data.

D (urine stream diameter): dynamic in a graph over time, in mm.

Davg: Average stream diameter.

Dmax: Maximum stream diameter.

Indication if split stream, plus how many sub-streams on average.

VL (urine stream velocity): dynamic in a graph over time, in cm/sec.

VLavg: Average velocity.

VLmax: Maximum velocity.

C (coefficient of percent fullness of the urine stream): dynamic in a graph over time.

Cavg: Average coefficient.

Cmax: Maximum coefficient.

Urine color (in a few pictures), with special indication if it includes blood or a high level of white particles.

Q (urine flow rate): dynamic in a graph over time in mL/sec.

Qavg: Average urine flow rate in mL/sec.

Qmax: Maximum urine flow rate in mL/sec.

TQmax: Time to maximum flow rate, in seconds.

VV: Voided Volume, in mL.

FT: Flow time, in seconds.

VT: Voiding Time, in seconds.

Intervals: How many voiding intervals occurred. If there was no break in the voiding then there was 1 interval, if there was 1 break then there were 2 intervals, etc.

If there were intervals, then VT is greater than FT.

The invention claimed is:

1. An in-toilet uroflowmetry device, whereby when installed in a toilet said device is not touched by a urine stream, and said toilet is usable for all normal functions by men and women, whereby said device comprises an open loop electronic belt, whereby said belt is attached by clips to the interior of the upper rim of the toilet bowl, said belt having:

a. at least two video cameras for taking video during urination;
   b. at least one motion sensor and at least one sound sensor for together controlling the activation and deactivation of said video cameras;
   c. at least two LEDs for providing lighting during urination;
   d. at least one light sensor for controlling said LEDs; and e. a Single Board Computer (SBC) for controlling all the device components and supporting wireless communication with a website, whereby said video is transferred to said SBC, and whereby said video is transferred wirelessly from said SBC to a website for performing image processing, said image processing comprising dynamically calculating the velocity, diameter and a coefficient C for said urine stream, whereby said velocity, diameter and a coefficient C are provided on said website and also used for dynamically computing flow rate of said urine stream.

2. The uroflowmetry device according to claim 1, further comprising one or more infrared video cameras.

3. The uroflowimetry device according to claim 1, wherein the LEDs are intensity-controlled LEDs.

4. A method of image processing according to claim 1, wherein the video on the website is comprised of a sequence of frames, said image processing calculates the following three values of the urine stream:
- a. Velocity of the urine stream, between each 2 consecutive video frames;
- b. Diameter of the urine stream, for each video frame; and,
- c. A coefficient C of the urine stream, for each video frame.

5. A method according to claim 4, wherein the computing includes the following three steps for each duration of between 0.05 second to 0.2 second:
- a. Computation of averages of the three values calculated by the image processing;
- b. Computation of the cross-sectional area of the urine stream, from the diameter; and
- c. Computation of flow rate from the cross-sectional area, velocity and the coefficient C of the urine stream.

* * * * *